(12) United States Patent
Bae

(10) Patent No.: US 12,118,147 B2
(45) Date of Patent: Oct. 15, 2024

(54) HAPTIC DEVICE BASED ON MULTIMODAL INTERFACE

(71) Applicant: WHOBORN INC., Seoul (KR)

(72) Inventor: Young Sik Bae, Seoul (KR)

(73) Assignee: WHOBORN INC., Seoul (KR)

( * ) Notice: Subject to any disclaimer, the term of this patent is extended or adjusted under 35 U.S.C. 154(b) by 18 days.

(21) Appl. No.: 17/845,170

(22) Filed: Jun. 21, 2022

(65) Prior Publication Data
US 2022/0326769 A1  Oct. 13, 2022

Related U.S. Application Data

(63) Continuation of application No. PCT/KR2020/019032, filed on Dec. 23, 2020.

(30) Foreign Application Priority Data

Dec. 23, 2019 (KR) .................. 10-2019-0173507
Dec. 23, 2019 (KR) .................. 10-2019-0173509

(51) Int. Cl.
| | |
|---|---|
| G06F 3/01 | (2006.01) |
| A43B 3/34 | (2022.01) |
| A43B 17/00 | (2006.01) |
| A61B 5/00 | (2006.01) |
| A61B 5/01 | (2006.01) |

(52) U.S. Cl.
CPC .............. G06F 3/014 (2013.01); A43B 3/34 (2022.01); A43B 17/00 (2013.01); A61B 5/015 (2013.01); A61B 5/6829 (2013.01); G06F 3/016 (2013.01)

(58) Field of Classification Search
CPC .. A43B 3/34; A43B 3/44; A43B 17/00; A43B 17/03; A61B 5/015; A61B 5/1036; A61B 5/11; A61B 5/112; A61B 5/6896; A61B 5/6807; A61B 5/6825; A61B 5/6829; G06F 3/011; G06F 3/014; G06F 3/016; G06F 3/017; G06F 3/0346; G06F 3/16; G06F 2203/0384

See application file for complete search history.

(56) References Cited

U.S. PATENT DOCUMENTS

| | | | |
|---|---|---|---|
| 9,173,596 B1* | 11/2015 | Berme | ............. A61B 5/0024 |
| 2008/0174550 A1* | 7/2008 | Laurila | ............. A63F 13/285 |
| | | | 345/158 |
| 2018/0188850 A1* | 7/2018 | Heath | ............. G06F 3/0202 |
| 2021/0165506 A1* | 6/2021 | Klein | ............. G06F 3/0346 |

* cited by examiner

*Primary Examiner* — Nitin Patel
*Assistant Examiner* — Cory A Almeida
(74) *Attorney, Agent, or Firm* — United One Law Group LLC; Kongsik Kim; Jhongwoo Peck

(57) ABSTRACT

A grippable haptic device includes an input device that receives a user input, a 9-axis sensor that detects movement of a hand of the user, a vibrator that provides a tactile sensation to the user, and a motion sensor that detects whether the user grips the grippable haptic device. An insole-type haptic device includes an input device that receives a user input, a plurality of 9-axis sensors that detect movement of a foot of the user, a vibrator that provides a tactile sensation to a sole of the foot of the user, and a plurality of pressure sensors that are distributed across the insole-type haptic device and measure a pressure exerted at each position of the sole of the user.

9 Claims, 10 Drawing Sheets

FIG. 2

| I/O | Command (MSB First 1Byte) | | | | | | | | Devices Count (MSB First 1Byte) | Devices Count (LSB First 1Byte) | Command (LSB First 1Byte) | | | | | | | |
|---|---|---|---|---|---|---|---|---|---|---|---|---|---|---|---|---|---|---|
| | I/O | Sight | Hearing | Touch | Smell | Taste | Reserve | Cmd Flag | 0x00 ~ 0xFF (max 255) | 0x00 ~ 0xFF (max 255) | Cmd Flag | Reserve | Taste | Smell | Touch | Hearing | Sight | I/O |
| INPUT 1 | 1 | x | x | x | x | x | x | 1 | n | reverse n | 1 | x | x | x | x | x | x | x |
| | | x | x | x | x | x | x | 0 | n | reverse n | 0 | x | x | x | x | x | x | x |
| OUTPUT 0 | 0 | x | x | x | x | x | x | 1 | n | reverse n | 1 | x | x | x | x | x | x | x |
| | | x | x | x | x | x | x | 0 | n | reverse n | 0 | x | x | x | x | x | x | x |

FIG. 3

| 0~n Device ID (2Bytes) | 0~n Packet Size (4Bytes) | Packet (Packet Size) | 0~n Packet Size (4Bytes) | 0~n Device ID (2Bytes) |
|---|---|---|---|---|
| (R)SHTSTR(R) + 0x00 ~ 0xFF Device Number | 0x00000000 ~ 0xFFFFFFFF bytes | Transfer Data Packet | 0x00000000 ~ 0xFFFFFFFF bytes | (R)SHTSTR(R) + 0x00 ~ 0xFF Device Number |
| 0xXX00 ~ 0xXXFF | Command Size | Device Input Initialize Command Packet Data | Command Size | 0xXX00 ~ 0xXXFF |
| 0xXX00 ~ 0xXXFF | Data Size | Device Input Packet Data | Data Size | 0xXX00 ~ 0xXXFF |
| 0xXX00 ~ 0xXXFF | Command Size | Device Output Initialize Command Packet Data | Command Size | 0xXX00 ~ 0xXXFF |
| 0xXX00 ~ 0xXXFF | Data Size | Device Output Packet Data | Data Size | 0xXX00 ~ 0xXXFF |

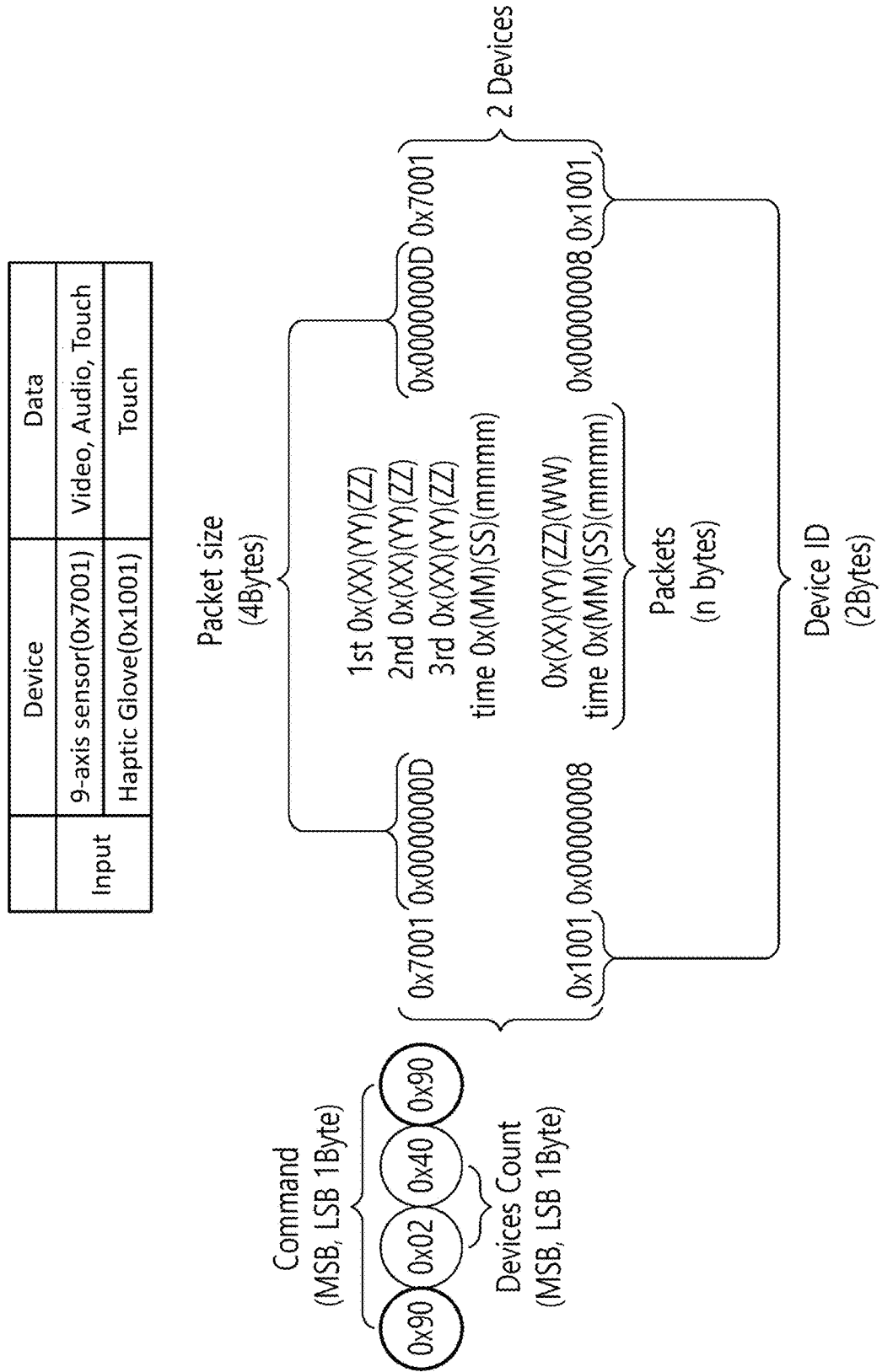

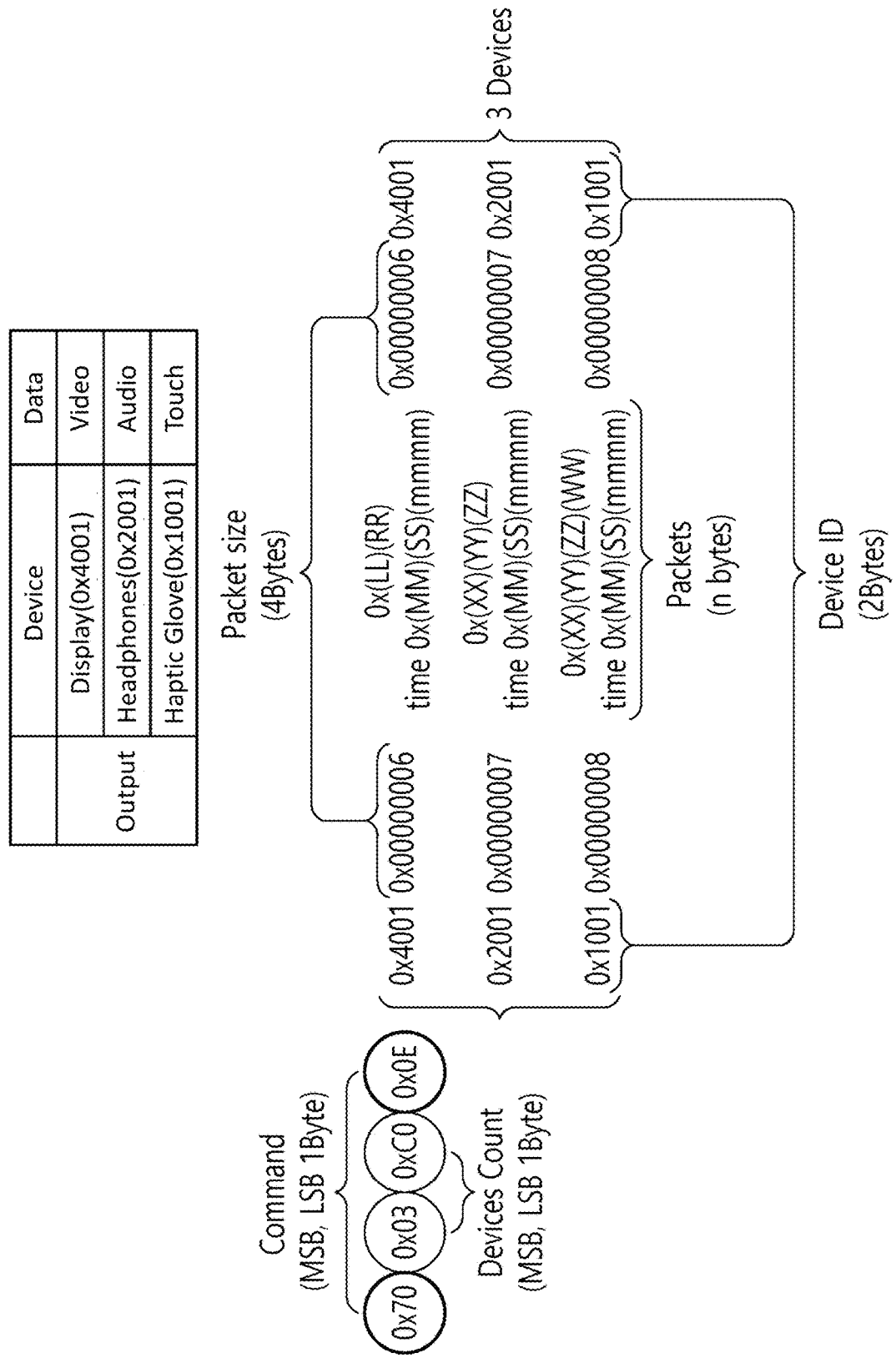

HAPTIC DEVICE BASED ON MULTIMODAL INTERFACE

CROSS-REFERENCE TO RELATED APPLICATION(S)

This application is a Continuation of PCT/KR2020/019032 filed on Dec. 23, 2020, which claims priority from Korean Application No. 10-2019-0173507 filed on Dec. 23, 2019 and Korean Application No. 10-2019-0173509 filed on Dec. 23, 2019. The aforementioned applications are incorporated herein by reference in their entireties.

TECHNICAL FIELD

The present disclosure relates to a haptic device based on a multimodal interface, and more particularly, to a haptic device based on a multimodal interface in the form of gloves and insoles of shoes.

BACKGROUND

Extended reality (eXtended Reality, XR) refers to a combination of virtual spaces created by computer technologies and wearable devices, and is a concept that includes virtual reality (VR), augmented reality (AR), and mixed reality (MR). With the growth of the XR market, the demand for multimodal systems that can input and reproduce data regarding the human senses is increasing. In particular, the multimodal system can be effectively used in various virtual training systems including medical fields such as surgery, defense fields such as shooting training or pilot training, and education fields such as teaching driving or musical instruments.

A multimodal system requires a haptic device to transmit human five senses to a user. Typical haptic devices include a hand grip type device that a user holds to use. However, the hand grip type device has a disadvantage that the user must continuously hold the controller with his/her hand, and functionally, it only detects the user's motion. Further, if it includes tactile reproduction functions, the price becomes very high.

On the other hand, there also exists haptic devices that can be worn on the foot, having the shape of a shoe. However, portability is reduced since the shape of the shoe is bulky, it cannot be manufactured to fit the shape of each user's foot, and functionally, it is limited to merely sensing the user's motion.

SUMMARY

An object of the present disclosure is to solve the above problems of the usability for a hand grip type haptic device and to provide a haptic device capable of reproducing a sense such as tactile sensation in addition to a user motion detection function.

Another object of the present disclosure is to provide an insole-type haptic device that can select coupling devices based on the purpose of the user, can be more easily carried due to a small form factor, can precisely detect user's motion and check the status of the user, and can reproduce a sense such as tactile sensation.

However, the problem to be solved by the present disclosure is not limited thereto, and may be variously expanded without departing from the spirit and scope of the present disclosure.

An aspect of the present disclosure provides a grippable haptic device configured to be attached to a glove or a hand of a user and to transmit a tactile sensation to the user based on extended reality (XR) contents, which may include an input device that receives a user input from the user, a 9-axis sensor that detects movement of the hand of the user, a vibrator that provides a tactile sensation to the user, a motion sensor that detects whether the user grips the grippable haptic device, a communication module that transmits and receives data between the grippable haptic device and an extended reality (XR) processor, and a power source that supplies electrical power to the grippable haptic device.

In some embodiments, the input device may be implemented as a button disposed on the grippable haptic device.

In some embodiments, the vibrator may provide the tactile sensation to the user by varying at least one of an intensity, a pattern, or a period of vibration according to the extended reality (XR) contents.

In some embodiments, the motion sensor may include a proximity sensor that measures a distance between fingers of the user and the grippable haptic device.

In some embodiments, the power source may include at least one of a battery or a body energy harvesting device.

In some embodiments, the grippable haptic device may have a substantially cylindrical shape to allow the user to grip it.

In some embodiments, the grippable haptic device may further include a temperature reproduction device that provides a predetermined temperature to the user.

A related aspect of the present disclosure provides an insole-type haptic device configured to be inserted into a shoe and worn by a user in order to deliver a tactile sensation to the user based on an extended reality (XR) contents, which may include an input device that receives a user input from the user, a plurality of 9-axis sensors that detect movement of a foot of the user, a vibrator that provides a tactile sensation to a sole of the foot of the user, and a plurality of pressure sensors that are distributed across the insole-type haptic device and measure a pressure exerted at each position of the sole of the foot of the user, a communication module that transmits and receives data between the insole-type haptic device and an extended reality (XR) processor, and a power source that supplies electrical power to the insole-type haptic device.

In some embodiments, the vibrator may include a plurality of vibration elements that form a vibration matrix.

In some embodiments, the insole-type haptic device may further include a pressure reproduction device, such that a pressurization medium may be injected into the pressure reproduction device based on pressure information for each position measured by the plurality of pressure sensors.

In some embodiments, the step of injecting the pressurization medium into the pressure reproducing device based on the pressure information for each position measured by the plurality of pressure sensors may include measuring the pressure at each position of the sole of the user, mapping the measured pressure information for each position, evaluating a degree of pressure balance of the foot of the user using the mapped pressure information for each position, and determining whether to inject the pressurization medium into the pressure reproduction device based on medical information of the user, and injecting the pressurization medium into the pressure reproduction device.

In some embodiments, the step of mapping the measured pressure information for each position may include mapping the measured pressure information for each position with respect to time.

In some embodiments, the step of evaluating the degree of pressure balance of the user's foot may include evaluating the degree of pressure balance considering motions of the user, which may include standing or walking.

In some embodiments, the medical information of the user may include at least one of a shape of the user's foot, a stride distance, or a walking posture, which may be obtained by analyzing the pressure information for each position.

In some embodiments, the step of determining whether to inject the pressurization medium into the pressure reproducing device based on medical information of the user may include determining a location and an injection amount for injecting the pressurization medium to allow the degree of pressure balance of the user to be improved.

In some embodiments, the step of injecting the pressurization medium into the pressure reproduction device based on the pressure information for each position measured by the plurality of pressure sensors may include checking whether the degree of pressure balance of the user is improved after the pressurization medium is injected.

In some embodiments, the power source may include at least one of a battery, a thermoelectric harvesting device, or a piezoelectric harvesting device.

In some embodiments, the insole-type haptic device may further include a temperature/humidity sensor that measures a temperature and/or a humidity inside the shoe.

In some embodiments, the insole-type haptic device may further include a temperature reproduction device that provides a predetermined temperature to the foot of the user.

The present disclosure may provide the following effects although it does not mean that a specific embodiment should include all of the following effects or only the following effects, so the scope of the disclosure should not be understood as being limited thereby.

The grippable haptic device according to the above-described embodiments of the present disclosure may solve the inconvenience in usability of the hand grip type haptic device in the related art and may reproduce a sense such as tactile sensation in addition to a user motion detection function.

In addition, the insole-type haptic device according to the above-described embodiments of the present disclosure may allow selection of coupled devices based on the purpose of the user, provide improved convenience for carrying due to the small form factor, provide more precise detection and status check of user's motion, reproduce a sense such as tactile sensation, and improve the user's balance using the pressure information from each position of the sole.

BRIEF DESCRIPTION OF THE DRAWINGS

FIGS. 2 and 3 show a protocol format in an extended reality system to which a haptic device based on a multimodal interface according to embodiments of the present disclosure can be applied;

FIG. 4 illustrates an input data format as an example of the protocol format of FIGS. 2 and 3;

FIG. 5 illustrates an output data format as an example of the protocol format of FIGS. 2 and 3;

DETAILED DESCRIPTION

Figure 1:
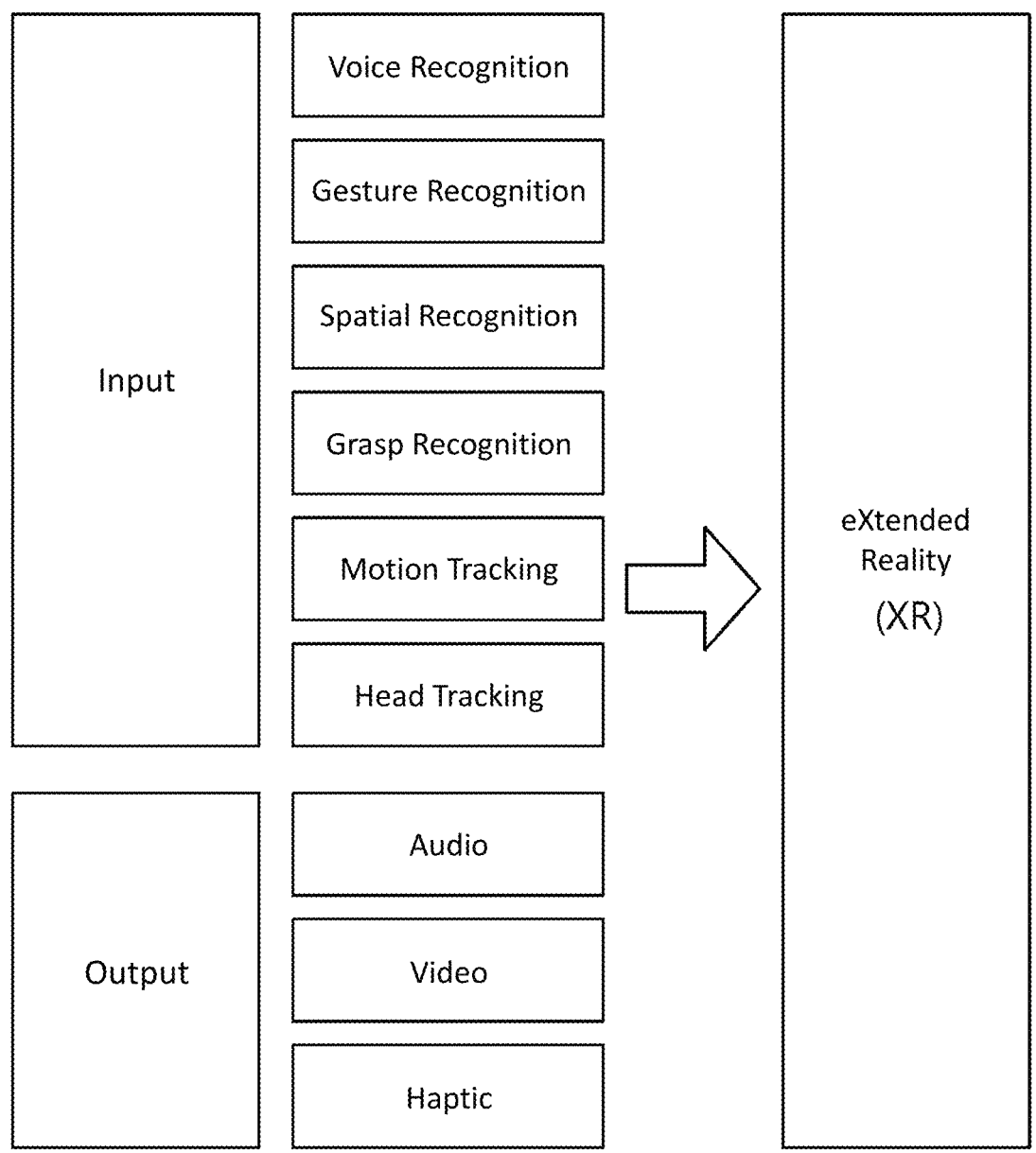
FIG. 1 schematically shows NFXM (NUI/NUX Format for XR Machine) for an extended reality system.

The present disclosure can have various modifications and various embodiments, and thus, specific embodiments will be illustrated in the drawings and described in detail.

However, this is not intended to limit the present disclosure to a specific embodiment, and it should be understood to include all modifications, equivalents and substitutes derived from the spirit and scope of the present disclosure.

Terms such as "first," "second," and the like may be used to describe various elements, but the elements should not be limited by the terms. These terms are used only for the purpose of distinguishing one component from another. For example, without departing from the scope of the present disclosure, a first component may be referred to as a second component, and similarly, a second component may also be referred to as a first component.

When a component is referred to as being "connected" to another component, it may be directly connected to the other component, but it should be understood that other components may exist in between. On the other hand, when it is mentioned that a certain element is "directly connected" to another element, it should be understood that no other element exists in between.

The terms used in the present application are only used to describe specific embodiments, and are not intended to limit the present disclosure. The singular expression includes the plural expression unless the context clearly dictates otherwise. In the present disclosure, terms such as "comprise" or "have" are intended to designate that a feature, number, step, operation, component, part, or combination thereof described in the specification exists, and it is to be understood that this does not preclude the possibility of addition or existence of one or more other features, numbers, steps, operations, components, parts, or combinations thereof.

Unless defined otherwise, all terms used herein, including technical and scientific terms, have the same meaning as commonly understood by one of ordinary skill in the art to which this disclosure pertains. Terms such as those defined in commonly used dictionaries should be interpreted as having a meaning consistent with the meaning in the context of the related art, and are not to be interpreted in an ideal or excessively formal meaning unless explicitly defined in the present disclosure.

Hereinafter, with reference to the accompanying drawings, exemplary embodiments of the present disclosure will be described clearly and in detail so that those of ordinary skill in the art can easily practice the present disclosure.

First, an extended reality system to which a haptic device based on a multimodal interface according to embodiments of the present disclosure can be applied will be described.

FIG. 1 schematically shows NFXM (NUI/NUX Format for XR Machine) for an extended reality system.

Referring to FIG. 1, NFXM may process input data associated with human five senses via voice recognition, gesture recognition, spatial recognition, grasp recognition, motion tracking, head tracking, or the like, and may provide extended reality (XR) to users by reproducing the human five senses via audio, video, haptics, or the like.

For example, the data collection of user behavior via NFXM may be performed with the following methods. The voice recognition may be processed using a voice analysis algorithm on the user's voice data that are inputted via a microphone, and the gesture recognition may be processed using a gesture analysis algorithm on the user's movement data that are inputted via a camera. The spatial recognition may be analyzed and processed using a camera and a spatial analysis algorithm, and the grasp recognition may be analyzed and processed using a MEMS (Micro Electro Mechanical System) device and a grasp analysis algorithm. The motion tracking may be analyzed and processed using a motion tracking algorithm on the data collected via a gyro sensor, and the head tracking may be processed using a head tracking algorithm on the data associated with the motion of user's head obtained with a gyro sensor and a compass sensor.

Reproduction of the five senses via NFXM may be performed with the following methods. The reproduction of the auditory senses may be provided by audio with three-dimensional and spatial sound having binaural effects that are outputted with dual speakers, and the reproduction of visual senses may be provided by a screen with a sense of reality and realism using a head mounted display (HMD) and extended reality (XR) technologies. The touch senses may be provided to the user with a tactile sensation based on the physical properties, shape, size, or the like of an object using techniques such as physical force, vibration, and pressure via a haptic device, and an object haptic algorithm.

FIGS. 2 and 3 show a protocol format in an extended reality system to which a haptic device based on a multimodal interface according to embodiments of the present disclosure may be applied.

Referring to FIGS. 2 and 3, the protocol format may have a mirror structure (Command MSB—Device Count MSB—Device Count LSB—Command LSB, Device ID—Packet size—Packets—Packet size—Device ID). The mirror structure may have a structure where the same data are transmitted twice, and it may ensure a high level of stability and reliability of communication by enabling comparison of the paired data among the data received during asynchronous communication between the computer and the extended reality (XR) output device and thereby performing data validation on its own.

One (1) byte may be allocated to the "Command," which represents information associated with the type of data. "I/O" may indicate whether the corresponding data is input data or output data, and may be represented as 1 for input data or as 0 for output data. The next five (5) bits may indicate with which sense the reproduction data included in the corresponding data are associated among "Sight," "Hearing," "Touch," "Smell," and "Taste." The "Reserve" bit may represent a reserved bit that may be used as needed. For example, the reserve bit may be used when reproduction data related to senses other than the five senses are included.

The command flag ("CmdFlag") may include information indicating whether or not reproduction data are allowed to be reproduced. Depending on the application, due to safety or security reasons, the extended reality (XR) system may need to be restricted so that the extended reality (XR) output device is prevented from reproducing the reproduction data even after receiving the reproduction data, or so that only particular users are allowed to reproduce the reproduction data. In some embodiments, it may be necessary to restrict reproduction data from being reproduced by a particular user on another user's output device. For example, if an extended reality (XR) system is used for surgical training, a professor may need to limit the haptic gloves worn by a student from moving outside of a specified location. To implement this feature, the command flag ("CmdFlag") may include information indicating whether the reproduction data is allowed to be reproduced so that the extended reality (XR) output device is allowed or not allowed to reproduce the reproduction data based on the command flag ("CmdFlag").

The device count ("Device Count") may indicate the number of devices to transmit/receive data, and one (1) byte may be allocated thereto.

The device identifier ("Device ID") may indicate which extended reality (XR) output device the data corresponds to, and two (2) bytes may be allocated thereto.

The packet size ("Packet Size") may indicate the size of a packet, and four (4) bytes may be allocated thereto.

A packet may include measurement data or reproduction data, and a time limit. In the case of input data (that is, when the I/O bit of the command is 1), the packet may include the measurement data that the measurement device (e.g., microphone, camera, MEMS device, etc.) transmits to the computer, and in the case of output data (that is, when the I/O bit of the command is 0), the packet may include the reproduction data to be reproduced by the output device.

Hereinbelow, the protocol format will be described with regard to two examples in FIGS. 4 and 5.

FIG. 4 illustrates an input data format as an example of the protocol format of FIGS. 2 and 3. Referring to FIG. 4, the displayed input data format may indicate that the input data include measurement data related to video, audio, and touch (0x90); that the input data are transmitted from two devices (0x02); that three pieces of measurement data and time information are transmitted from a 9-axis sensor (0x7001); and that one piece of measurement data and time information are transmitted from a haptic glove (0x1001).

FIG. 5 illustrates an output data format as an example of the protocol format of FIGS. 2 and 3. Referring to FIG. 5, the displayed output data format may indicate that the output data include reproduction data related to video, audio, and touch (0x70); that the output data are transmitted to three devices (0x03); that a display (0x4001) reproduces the reproduction data related to the video within a time limit; that headphones (0x2001) reproduce the reproduction data related to the audio within a time limit; and that a haptic glove (0x1001) reproduces the reproduction data related to the touch within a time limit.

Figure 6:
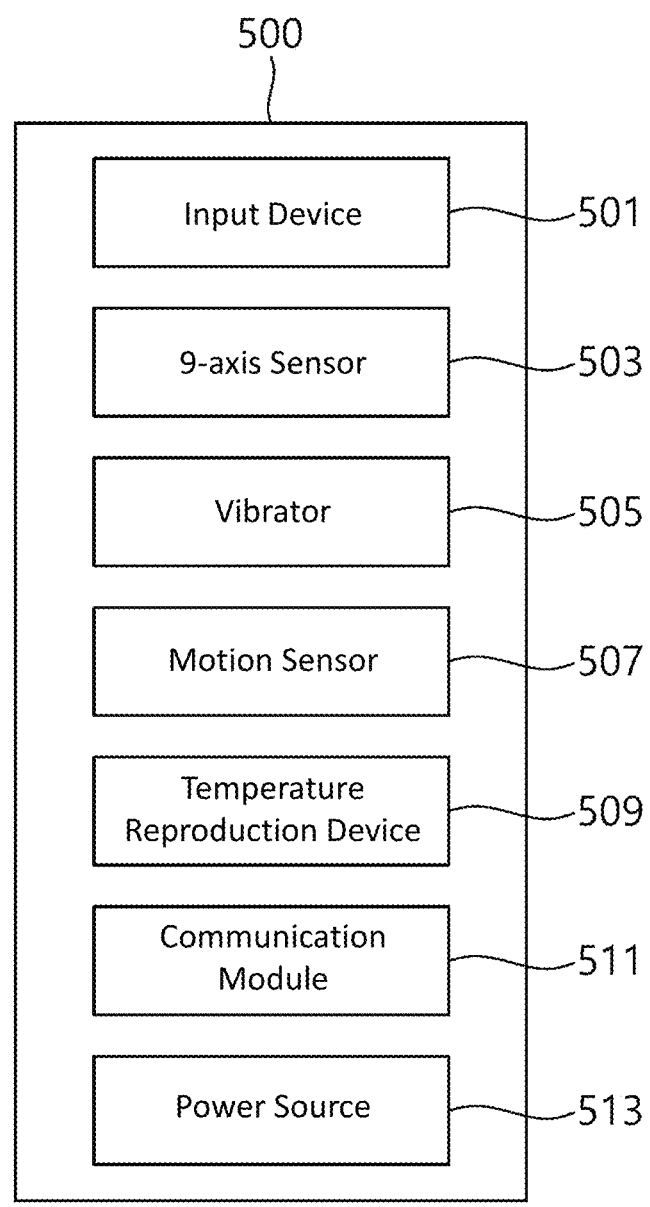
FIG. 6 is a block diagram of a stationary haptic device according to an embodiment of the present disclosure.
Figure 7:
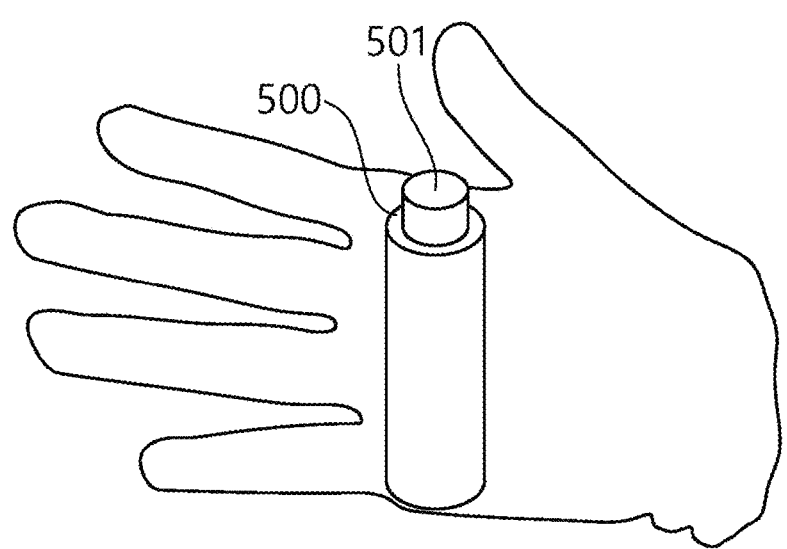
FIG. 7 is an exemplary view in which the stationary haptic device according to an embodiment of the present disclosure is attached to a glove.

FIG. 6 is a block diagram of a stationary haptic device according to an embodiment of the present disclosure, and FIG. 7 is an exemplary view in which the stationary haptic device according to an embodiment of the present disclosure is attached to a glove.

Referring to FIG. 6, a grippable haptic device 500 according to an embodiment of the present disclosure may include an input device 501, a 9-axis sensor 503, a vibrator 505, a motion sensor 507, and a temperature reproduction device 509, a communication module 511, and a power source 513.

The input device 501 may receive a user input from a user. For example, the input device 501 may include a button disposed on the top of the grippable haptic device 500. By pressing the button, the user may make an appropriate input according to the current contents of the extended reality (XR).

The 9-axis sensor 503 may detect the movement of the user's hand. For example, the 9-axis sensor 503 may detect a change in the orientation angle and location of the user's hand.

The vibrator 505 may transmit a tactile sensation to the user. The vibrator 505 may be implemented as a device that transmits a tactile sensation via a physical or electrical means, and may be implemented with, for example, a vibration motor, a vibration element using ultrasonic waves, or a vibration element using an electric signal. The vibrator 505 may transmit the tactile sensation to the user by varying the intensity, pattern, and/or period of vibration according to the contents of the extended reality (XR).

The motion sensor 507 may detect whether the user grips the grippable haptic device 500. The motion sensor 507 may include a proximity sensor that detects the gripping based on the distance between the user's fingers and the grippable haptic device 500. For example, in the case of virtual training for tennis or cooking using extended reality (XR), in response to the user gripping the grippable haptic device 500, the motion sensor 507 may detect such a motion and it may be recognized that the user grabs a tennis racquet or a cooking utensil in the virtual reality.

The temperature reproduction device 509 may provide a predetermined temperature to the user. The temperature reproduction device 509 may heat the grippable haptic device 500 based on an exothermic reaction, and may cool the grippable haptic device 500 based on an endothermic reaction. The temperature reproduction device 509 may reproduce a required temperature according to the contents of the extended reality (XR). For example, the temperature reproduction device 509 may be implemented with an element having a thermoelectric effect, and may include any device capable of varying the temperature based on a command by the extended reality (XR) processor.

The communication module 511 may transmit and receive data between the grippable haptic device 500 and the extended reality (XR) processor. The communication module 511 may use wireless communication to transmit the user input from the input device 501, such as the movement of the user's hand from the 9-axis sensor 503, gripping action from the motion sensor 507, and the like, to the extended reality (XR) processor. Further, the communication module 511 may receive tactile data according to the extended reality (XR) contents from the extended reality (XR) processor. The extended reality (XR) processor may be configured to generate tactile data and deliver them to the user after processing the extended reality (XR) contents based on the user input, the movement of the hand, and the gripping action received from the grippable haptic device 500.

The power source 513 may supply electrical power to the grippable haptic device 500. The power source 513 may be at least one of a battery or a body energy harvesting device. The body energy harvesting device may be a device capable of generating energy using a temperature difference or a position change due to the user's movement. Accordingly, with the body energy harvesting device, the grippable haptic device 500 may operate without a battery.

Referring to FIG. 7, the grippable haptic device 500 may be formed in a substantially cylindrical shape and may be used as being attached to a glove. A user may wear a glove to which the grippable haptic device 500 is attached, and then may enter a user input via the input device 501 according to extended reality (XR) contents or may feel the tactile sensation transmitted by the grippable haptic device 500. Conventional hand grip type devices in the related art have a problem that the user must continuously hold the controller with his or her hand. However, since the haptic device 500 according to the present disclosure is not required to be gripped continuously, but rather needs to be gripped whenever necessary, the user may avoid discomfort and the user experience (UX) may be improved.

Further, instead of the motion sensor 507 included in the grippable haptic device 500 in FIG. 6, a plurality of sensors may be provided in the glove shown in FIG. 7. Accordingly, the state of the user's hand (e.g., fingers are extended, fingers are bent to grip the grippable haptic device 500, etc.) may be sensed.

Figure 8:
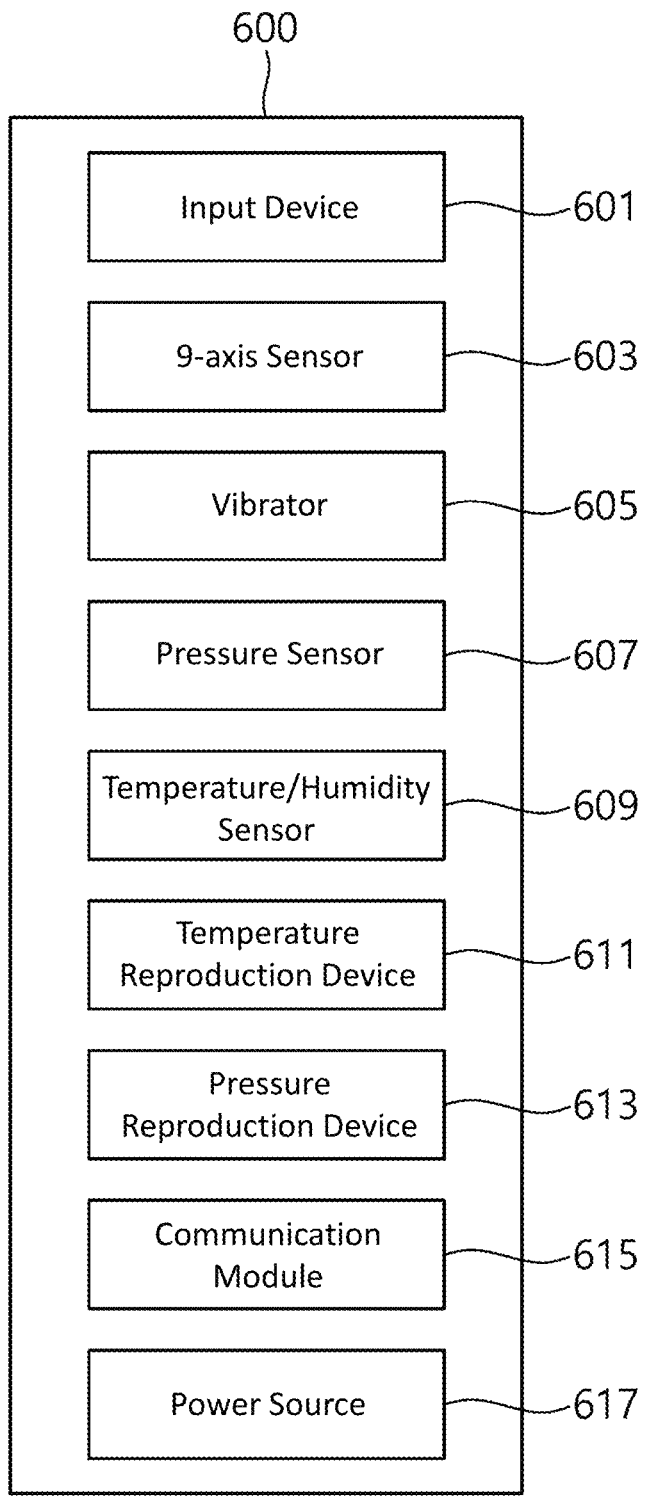
FIG. 8 is a block diagram of an insole-type haptic device according to an embodiment of the present disclosure.
Figure 9:
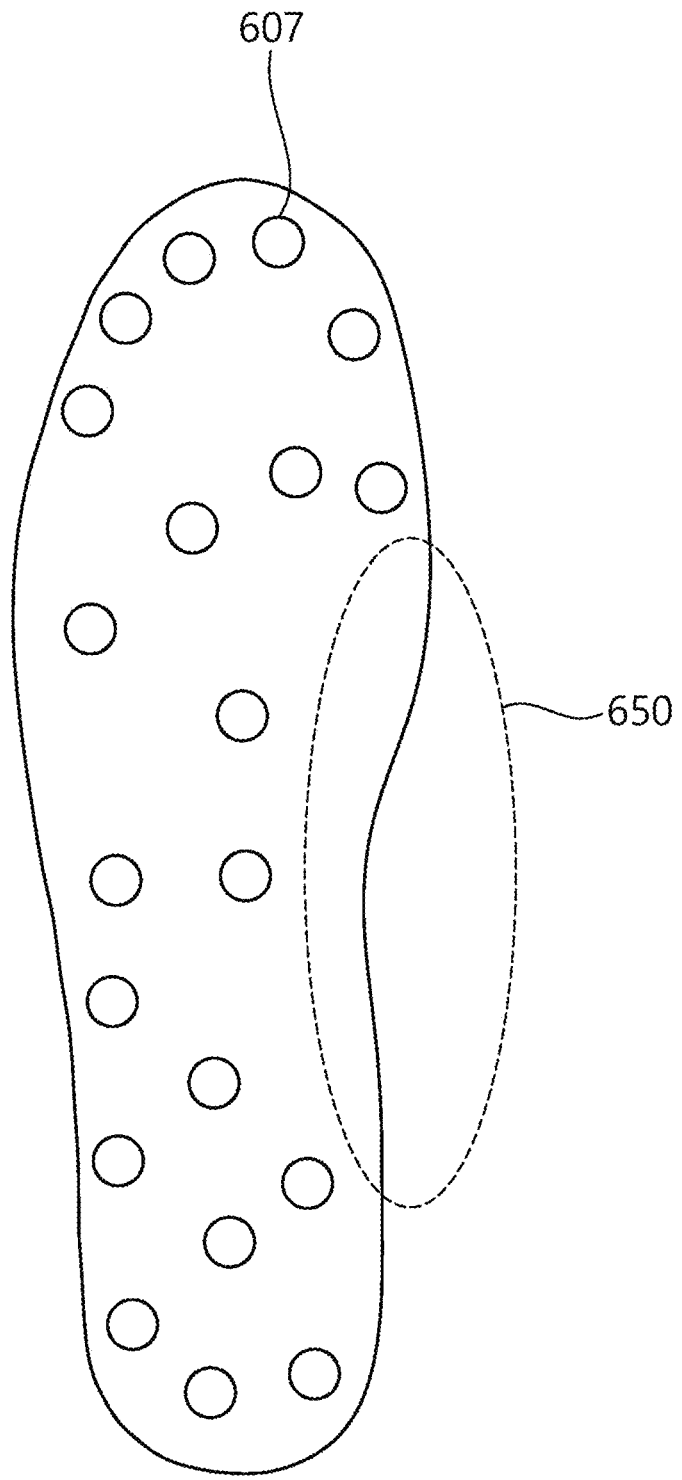
FIG. 9 shows an exemplary arrangement of pressure sensors in an insole-type haptic device according to an embodiment of the present disclosure.

FIG. 8 is a block diagram of an insole-type haptic device according to an embodiment of the present disclosure, and FIG. 9 shows an exemplary arrangement of pressure sensors in the insole-type haptic device.

Referring to FIG. 8, an insole-type haptic device 600 according to an embodiment of the present disclosure may include an input device 601, a 9-axis sensor 603, a vibrator 605, a pressure sensor 607, a temperature/humidity sensor 609, a temperature reproduction device 611, a pressure reproduction device 613, a communication module 615, and a power source 617. Components in the insole-type haptic device 600 that function similarly as the corresponding components of the grippable haptic device 500 described above will be omitted.

The 9-axis sensor 603 may detect the movement of the user's foot. For example, the insole-type haptic device 600 may include two 9-axis sensors 603 respectively disposed at the front portion and the back portion of the insole. Due to such a configuration, the position and the movement direction of the user's foot may be determined.

The vibrator 605 may transmit a tactile sensation to the sole of the user's foot. The vibrator 605 may be implemented with a device that transmits a tactile sensation by a physical or electrical means, and may include, for example, a vibration motor, a vibration element using ultrasonic waves, or a vibration element using an electric signal. The vibrator 605 may include a plurality of vibration elements to establish a vibration matrix. The vibrator 605 may transmit the tactile sensation to the user by varying the intensity, pattern, location, and/or period of vibration according to the contents of the extended reality (XR). Accordingly, the user may sense the material, shaking, inclination, or the like of the ground by the tactile sensation transmitted from the vibrator 605.

The pressure sensor 607 may measure the pressure applied to the sole of the user's foot. The insole-type haptic device 600 may include a plurality of pressure sensors 607 distributed across the entire insole, as shown in FIG. 9. Using the pressures measured by the pressure sensor 607 and the movement of the foot determined by the 9-axis sensor 603, the direction in which the user's foot moves and the position of the foot may be sensed. The insole-type haptic device 600 may inject a pressurization medium into the pressure reproduction device 613 based on the pressures measured at each position by the pressure sensors 607 to suit the user's foot shape, thereby providing the effects such as facilitating more comfortable walking for the user, reducing fatigue, providing posture correction, and the like. Improving the user's balance will be described later below with reference to FIG. 10.

The temperature/humidity sensor 609 may measure the temperature and/or humidity inside the shoe. The insole-type haptic device 600 may use the temperature and humidity information measured by the temperature/humidity sensor 609 to check the status of the user's feet, and may issue a warning signal to the user that the user is recommended to take off the shoes and take a rest when the temperature or humidity is high.

The temperature reproduction device 611 may provide a predetermined temperature to the user. The temperature reproduction device 611 may heat the insole-type haptic device 600 through an exothermic reaction, and may cool the insole-type haptic device 600 through an endothermic reaction. The temperature reproduction device 611 may reproduce the required temperature according to the extended reality (XR) contents, and may reproduce the required temperature based on the temperature inside the shoe measured by the temperature/humidity sensor 609. For example, the temperature reproduction device 509 may be implemented with a device having a thermoelectric effect, and may include any device capable of generating a temperature based on the commands from the extended reality (XR) processor.

The pressure reproduction device 613 may provide pressure to the sole of the user's foot by injecting a medium for pressurization. The medium for pressurization may be a gas (e.g., air) or liquid (e.g., water, oil), which is a material capable of applying pressure to the sole of the user's foot when injected into the pressure reproduction device 613. The pressure reproduction device 613 may be integrally configured, or may be configured in a matrix form to allow a position to which the pressurization medium is to be injected to be determined based on the user's pressure balance. In particular, the pressure reproduction device 613 may inject the pressurization medium in an arch region 650 shown in FIG. 9 as well as other regions across the entire sole. Maintaining adequate pressure level at the arch region 650 plays an important role in reducing foot fatigue and helping the user to maintain good posture.

The power source 617 may supply electrical power to the insole-type haptic device 600. The power source 617 may be at least one of a battery, a thermoelectric harvesting device, or a piezoelectric harvesting device. The thermoelectric harvesting device may be a device that generates energy with the temperature generated in the shoe, and the piezoelectric harvesting device may be a device that generates energy with the pressure exerted by the user's feet. With the thermoelectric harvesting device and the piezoelectric harvesting device, the insole-type haptic device 600 may operate even without a battery.

Figure 10:
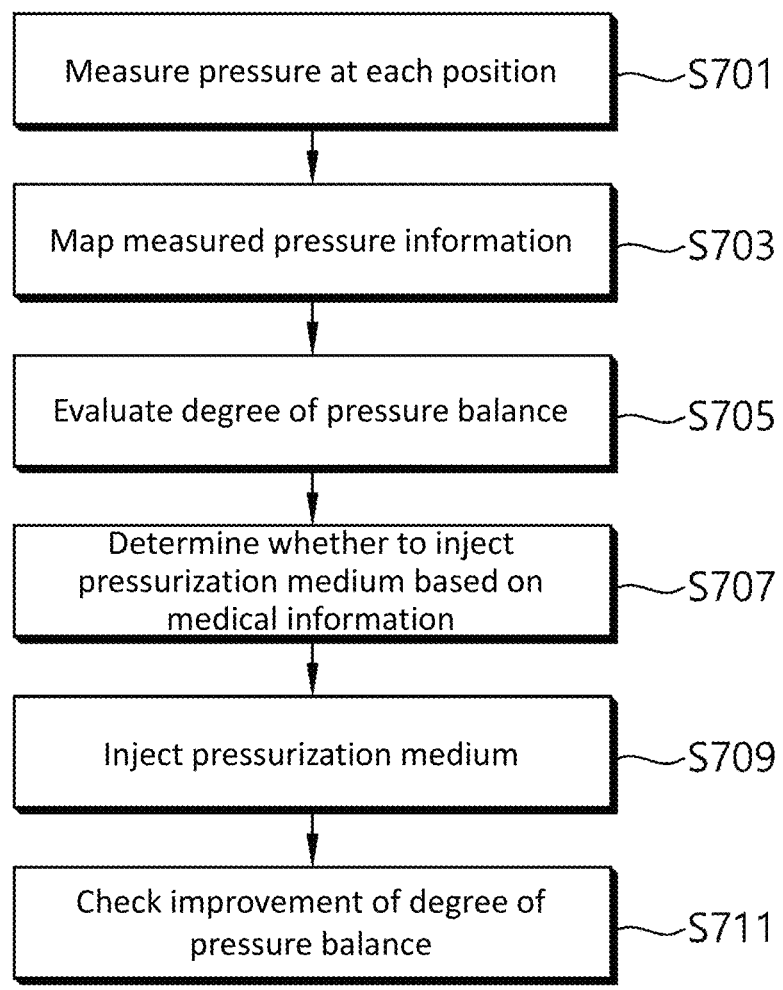
FIG. 10 is a flowchart of a method for improving a user's balance by using pressure information by an insole-type haptic device according to an embodiment of the present disclosure.

FIG. 10 is a flowchart of a method for improving a user's balance using the pressure information by an insole-type haptic device according to an embodiment of the present disclosure.

Referring to FIG. 10, in step S701, the pressure for each position of the user's sole may be measured. As described above, the insole-type haptic device 600 may measure the pressure for each position of the user's sole of the foot using a plurality of pressure sensors 607 distributed across the entire insole.

In step S703, the measured pressure information for each position may be graphed (e.g., mapped). Here, the graph may be in a 3D image form. In some embodiments, by segmenting the pressure information for each position with respect to time and mapping it with respect to time, the change in pressure on the sole of the foot may be determined in the graph when the user is standing or walking.

In step S705, the degree of pressure balance of the user's foot may be calculated using the mapping of step S703. The degree of pressure balance may indicate whether appropriate pressure is being applied for each position of the user's feet, and it may check whether the user's standing posture is correct or whether the user's gait is balanced by using the degree of pressure balance. If the pressure information is segmented with respect to time and mapped in step S703, it may be checked whether the user is maintaining the balance, considering the user's motion (e.g., standing, walking, etc.).

In step S707, it may be determined whether the pressurization medium is to be injected into the pressure reproduction device 613 using the user's medical information. Herein, the user's medical information may include the shape of the user's foot (e.g., normal foot, flat foot, concave foot, etc.), stride length, walking posture, or the like. The user's medical information may be obtained by analyzing the pressure information for each position measured in step S701. In step S707, when it is determined that the injection of the pressurization medium is necessary, the location and the amount of injection of the pressurization medium may be determined together to improve the user's balance. As discussed above, the arch region 650 may play an important role to improve the user's balance and posture, thus, in step S707, the amount of injection of the pressurization medium at the arch region 650 may be determined.

In step S709, the pressurization medium may be injected into the pressure reproduction device 613 based on the determination result in step S707. In step S711, it may be checked whether the user's balance is improved after the pressurization medium is injected. If the balance is not improved even after injection of the pressurization medium, the process may return to step S701 and repeat the subsequent steps by re-measuring the pressure for each position of the sole with the pressurization medium injected.

Although the description is given above with reference to the drawings and embodiments, the scope of the present disclosure is not limited to the described drawings or embodiments. Those skilled in the art will appreciate the spirit and scope of the present disclosure described in the claims below. It will be understood that various modifications and variations of the present disclosure can be made without departing from the scope thereof.

What is claimed is:

1. A grippable haptic device configured to transmit a tactile sensation to the user according to extended reality (XR) contents, comprising:
    an input device that receives a user input from the user;
    a 9-axis sensor that detects movement of the hand of the user;
    a vibrator that provides a tactile sensation to the user;
    a motion sensor that detects whether the user grips the grippable haptic device;
    a communication module that transmits and receives data between the grippable haptic device and an extended reality (XR) processor in accordance with a protocol format; and
    a power source that supplies electrical power to the gripped haptic device,
    wherein the grippable haptic device has a substantially cylindrical shape and is attached to a glove, and
    wherein the protocol format has a mirror structure where same data are transmitted twice, enabling comparison of paired data among the data received during asynchronous communication between the grippable haptic device and the XR processor for data validation.

2. The grippable haptic device according to claim 1, wherein the input device is implemented as a button disposed on the grippable haptic device.

3. The grippable haptic device according to claim 1, wherein the vibrator provides the tactile sensation to the user by varying at least one of an intensity, a pattern, or a period of vibration according to the extended reality (XR) contents.

4. The grippable haptic device according to claim 1, wherein the motion sensor includes a proximity sensor that measures a distance between fingers of the user and the grippable haptic device.

5. The grippable haptic device according to claim 1, wherein the power source comprises at least one of a battery or a body energy harvesting device.

6. The grippable haptic device according to claim 1, further comprising:
   a temperature reproduction device that provides a predetermined temperature to the user.

7. The grippable haptic device according to claim 1, wherein the mirror structure includes Command MSB-Device Count MSB-Device Count LSB-Command LSB, Device ID-Packet size-Packets-Packet size-Device ID.

8. The grippable haptic device according to claim 7, wherein the Command includes a command flag (CmdFlag) that indicates whether or not reproduction data are allowed to be reproduced.

9. The grippable haptic device according to claim 8, wherein the grippable haptic device is used for training purposes, and
   wherein a trainer is allowed to limit the grippable haptic device worn by a trainee from moving outside of a specified location based on the command flag.

* * * * *